US008076124B2

(12) United States Patent
McKnight et al.

(10) Patent No.: US 8,076,124 B2
(45) Date of Patent: Dec. 13, 2011

(54) METHOD AND APPARATUS FOR SUSTAINING VIABILITY OF BIOLOGICAL CELLS ON A SUBSTRATE

(75) Inventors: Timothy E. McKnight, Greenback, TN (US); Anatoli V. Melechko, Oak Ridge, TN (US); Michael L. Simpson, Knoxville, TN (US)

(73) Assignee: UT-Battelle, LLC, Oak Ridge, TN (US)

( * ) Notice: Subject to any disclaimer, the term of this patent is extended or adjusted under 35 U.S.C. 154(b) by 1007 days.

(21) Appl. No.: 11/624,040

(22) Filed: Jan. 17, 2007

(65) Prior Publication Data

US 2008/0171386 A1 Jul. 17, 2008

(51) Int. Cl.
*C12M 3/00* (2006.01)

(52) U.S. Cl. ........................ 435/285.1; 850/58; 977/876

(58) Field of Classification Search ........................ None
See application file for complete search history.

(56) References Cited

U.S. PATENT DOCUMENTS

| | | | | |
|---|---|---|---|---|
| 5,457,041 | A | 10/1995 | Ginaven et al. | |
| 6,479,028 | B1 * | 11/2002 | Kaner et al. | 423/414 |
| 6,713,519 | B2 | 3/2004 | Wang et al. | |
| 6,958,216 | B2 | 10/2005 | Kelley et al. | |
| 6,982,519 | B2 | 1/2006 | Guillorn et al. | |
| 2002/0175323 | A1 | 11/2002 | Guillom et al. | |
| 2002/0193729 | A1 | 12/2002 | Cormier et al. | |
| 2003/0228695 | A1 | 12/2003 | Nakamura et al. | |
| 2004/0063100 | A1 | 4/2004 | Wang | |
| 2004/0076681 | A1 | 4/2004 | Dennis et al. | |
| 2004/0197909 | A1 | 10/2004 | Mcknight et al. | |
| 2005/0176245 | A1 | 8/2005 | Melechko et al. | |

FOREIGN PATENT DOCUMENTS

| | | |
|---|---|---|
| WO | WO 00/20554 | 4/2000 |
| WO | WO 01/67821 A1 | 9/2001 |

OTHER PUBLICATIONS

McKnight et al., Tracking Gene Expression After DNA Delivery Using Spatially Indexed Nanofiber Arrays, Nanoletters, 2004, vol. 4, No. 7, pp. 1213-1219.
Cai et al., Carbon Nanotube-Enhanced Electrochemical DNA Biosensor for DNA Hybridization Detection, Anal Bioanal Chem, 2003, vol. 375, pp. 287-293.
Martin C.R. et al., "The Emerging Field of Nanotube Biotechnology", *Nature Reviews Drug Discovery 2*:29-37 (2003).
Oupicky D. et al., "Laterally Stabilized Complexes of DNA with Linear Reducible Polycations: Strategy for Triggered Intracellular Activation of DNA Delivery Vectors", *J. Am. Chem. Soc. 124*(1):8-9 (2002).
Lemieux P. et al., "Block and Graft Copolymers and NanoGel Copolymer Networks for DNA Delivery into Cell", *J. Drug Target 8*(2):91-105 (2000) (Abstract p. 1-2).
Revzin A. et al., "Fabrication of Poly(Ethylene Glycol) Hydrogel Microstructures Using Photolithography", *Langmuir 17*(18):5440-5447 (2001) (Abstract p. 1).
Hafner J.H. et al., "Structural and Functional Imaging with Carbon Nanotube AFM Probes", *Progress in Biophysics & Molecular Biology 77*:73-110 (2001).
Hu W. et al., "Fabrication and Characterization of Vertically Aligned Carbon Nanotubes on Silicon Substrates Using Porous Alumina Nanotemplates", *Journal of Nanoscience and Nanotechnology 2*(2):203-207 (2002).
Wong S.S. et al., "Convalently Functionalized Nanotubes as Nanometre-Sized Probes in Chemistry and Biology", *Nature 394*:52-55 (1998).
Li W.Z. et al., "Large-Scale Synthesis of Aligned Carbon Nanotubes", *Science 274*:1701-1703 (1996).
Sotiropoulou S. et al., "Carbon Nanotube Array-Based Biosensor", *Anal Bioanal Chem 375*:103-105 (2003).
Ren Z.F. et al., "Synthesis of Large Arrays of Well-Aligned Carbon Nanotubes on Glass", *Science 282*:1105-1107 (1998).
Cai H. et al., "Carbon Nanotube-Enhanced Electrochemical DNA Biosensor for DNA Hybridization Detection", *Anal Bioanal Chem. 375*:287-293 (2003).
Endy D. et al., "Modelling Cellular Behaviour", *Nature 409*:391-395 (2001).
Hasty J. et al., "Engineered Gene Circuits", *Nature 420*:224-230 (2002).
Gardner T.S. et al., "Construction of a Genetic Toggle Switch is *Escherichia coli", Nature 403*:339-342 (2000).
Elowitz M.B. et al., "A Synthetic Oscillatory Network of Transcriptional Regulators", *Nature 403*:335-338 (2000).
Guet C.C. et al., "Combinatorial Synthesis of Genetic Networks", *Science 296*:1466-1470 (2002).
Simpson M.L. et al., "Whole-Cell Biocomputing", *TRENDS in Biotechnology 19*(8):317-323 (2001).
Chan W.C.W. et al., "Quantum Dot Bioconjugates for Ultrasensitive Nanisotopic Detection", *Science 281*:2016-2018 (1998).
Bruchez, Jr. M. et al., "Semiconductor Nanocrystals as Fluorescent Biological Labels", *Science 281*:2013-2016 (1998).
Dubertret B. et al., "In Vivo Imaging of Quantum Dots Encapsulated in Phospholipid Micelles", *Science 298*:1759-1762 (2002).
Wightman R.M. et al., "Temporally Resolved Catecholamine Spikes Correspond to Single Vesicle Release from Individual Chromaffin Cells", *Proc. Natl. Acad. Sci. USA 88*:10754-10758 (1991).
Knoblauch M. et al., "A Galinstan Expansion Femtosyringe for Microinjection of Eukaryotic Organelles and Prokaryotes", *Nature Biotechnology 17*:906-909 (1999).
McAllister D.V. et al., "Microfabricated Microneedles for Gene and Drug Delivery", *Annu. Rev. Biomed. Eng. 02*:289-313 (2000).

(Continued)

*Primary Examiner* — Jim Ketter
(74) *Attorney, Agent, or Firm* — Scully, Scott, Murphy & Presser, P.C.

(57) ABSTRACT

A method for the transient transformation of a living biological cell having an intact cell membrane defining an intracellular domain, and an apparatus for the transient transformation of biological cells. The method and apparatus include introducing a compartmentalized extracellular component fixedly attached to a cellular penetrant structure to the intracellular domain of the cell, wherein the cell is fixed in a predetermined location and wherein the component is expressed within in the cell while being retained within the compartment and wherein the compartment restricts the mobility and interactions of the component within the cell and prevents transference of the component to the cell.

23 Claims, 7 Drawing Sheets

OTHER PUBLICATIONS

Woolley A.T. et al., "Direct Haplotyping of Kilobase-Size DNA Using Carbon Nanotube Probes", *Nature Biotechnology 18*:760-763 (2000).

Guillorn M.A. et al., "Individually Addressable Vertically Aligned Carbon Nanofiber-Based Electrochemical Probes", *Journal of Applied Physics 91*(6):3824-3828 (2002).

Kim P. et al., "Nanotube Nanotweezers", *Science 286*:2148-2150 (1999).

Merkulov V.I. et al., "Patterned Growth of Individual and Multiple Vertically Aligned Carbon Nanofibers", *Applied Physics Letters 76*(24):3555-3557 (2000).

Merkulov V.I. et al., "Shaping Carbon Nanostructures by Controlling the Synthesis Process", *Applied Physics Letters 79*(8):1178-1180 (2001).

Cong B. et al., "Natural Alleles at a Tomato Fruit Size Quantitative Trait Locus Differ by Heterochronic Regulatory Mutations", *PNAS 99*(21):13606-13611 (2002).

Dwyer C. et al., "DNA-Functionalized Single-Walled Carbon Nanotubes", *Nanotechnology 13*:601-604 (2002).

Nguyen C.V. et al., "Preparation of Nucleic Acid Functionalized Carbon Nanotube Arrays", *Nano Letters 2*(10):1079-1081 (2002).

Hsie A.W. et al., "The Use of Chinese Hamster Ovary Cells to Quantify Specific Locus Mutation and to Determine Mutagenicity of Chemicals", *Mutation Research 86*:193-214 (1981).

Merkulov V.I. et al., "Effects of Spatial Separation on the Growth of Vertically Aligned Carbon Nanofibers Produced by Plasma-Enhanced Chemical Vapor Deposition", *Applied Physics Letters 80*(3):476-478 (2002).

Brown G.M. et al., "Electrochemically Induced Adsorption of Radio-Labeled DNA on Gold and HOPG Substrates for STM Investigations", *Ultramicroscopy 38*:253-264 (1991).

Hamad-Schifferli K. et al., "Remote Electronic Control of DNA Hybridization Through Inductive Coupling to an Attached Metal Nanocrystal Antenna", *Nature 415*:152-155 (2002).

Luo D. et al., "Synthetic DNA Delivery Systems", *Nature Biotechnology 18*:33-37 (2000).

Filion M.C. et al., "Major Limitations in the Use of Cationic Liposomes for DNA Delivery", *International Journal of Pharmaceutics 162*:159-170 (1998).

Merkulov V.I. et al., "Alignment Mechanism of Carbon Nanofibers Produced by Plasma-Enhanced Chemical-Vapor Deposition", *Applied Physics Letters 79*(18):2970-2972 (2001).

Arbault S. et al., "Activation of the NADPH Oxidase in Human Fibroblasts by Mechanical Intrusion of a Single Cell with an Ultramicroelectrode", *Carcinogenesis 18*(3):569-574 (1997).

Desai T.A. et al., "Micromachined Interfaces: New Approaches in Cell Immunoisolation and Biomolecular Separation", *Biomolecular Engineering 17*:23-36 (2000).

Merkulov V.I. et al., "Field Emission Properties of Different Forms of Carbon", *Solid-State Electronics 45*:949-956 (2001).

Ziauddin J. et al., "Microarrays of Cells Expressing Defined cDNAs", *Nature 411*:107-110 (2001).

Merkulov V.I. et al., "Field-Emission Studies of Smooth and Nanostructured Carbon Films", *Applied Physics Letters 75*(9):1228-1230 (1999).

International Search Report and Written Opinion of the International Searching Authority, PCT/US2004/010512, Oct. 12, 2004.

Han S W et al., "A molecular deliver system by using AFM and nanoneedle", Biosensors and Bioelectronics, Apr. 15, 2005, pp. 2120-2125, vol. 20, No. 10, Elsevier Science Publishers, Barking, Great Britain.

Han S et al., "Gene expression using an ultrathin needle enabling accurate displacement and low invasiveness", Biochemical and Biophysical Research Communications, Jul. 8, 2005, pp. 633-639, vol. 332, No. 3, Academic Press Inc, Orlando, Florida, USA.

* cited by examiner

METHOD AND APPARATUS FOR SUSTAINING VIABILITY OF BIOLOGICAL CELLS ON A SUBSTRATE

The United States Government has rights in this invention pursuant to contract no. DE-AC05-00OR22725 between the United States Department of Energy and UT-Battelle, LLC.

TECHNICAL FIELD

The disclosure relates generally to the fields of nanotechnology and biotechnology. Specifically, the disclosure relates a method for the transient transformation of a biological cell via introduction of a compartmentalized exogenous component to the intracellular domain of the cell, and a substrate suitable for such transformation. The disclosure also relates a method for the substrate mediated delivery of compartmentalized exogenous material to a biological cell.

BACKGROUND AND SUMMARY

Some biological cells, either by natural mutation or through genetic engineering, lack specific enzymes required for either synthesizing an essential molecule or breaking down a toxic molecule. These cells, known as auxotrophs or auxotrophic organisms, are generally cultured with the nutrients that they require for survival. They can also be enabled to survive by providing either the deficient enzyme itself or a copy of the DNA coding for the deficient enzyme to the intracellular domain of the cell. A cell having all of the required metabolic machinery for survival is known as a prototroph, or a prototrophic organism.

For the purposes of this disclosure, the terms “auxotrophic” and “auxotroph” are used to signify living cells that are lacking one or more particular enzymes in a metabolic pathway critical for survival of the cell in the desired environmental conditions. The terms “prototrophic” and “prototroph” are used to signify living cells capable of survival in the desired environmental conditions without modification. Thus, “prototroph” is an antonym of “auxotroph.”

In some applications using genetically modified cells or organisms, it is important to limit the escape potential of the cell or organism. Often auxotrophic systems are used for such applications. For example, the use of genetically modified organisms in field applications requires mechanisms that are designed to limit the escape potential of the genetically modified cells or their modified DNA into the gene pool of the natural ecosystem. One mechanism for limiting the escape potential of auxotrophic cells to the surrounding ecosystem is to provide an essential nutrient for use by the cells that is not found in the local environment. This allows a zone of survival for the auxotrophic cells around the point of administration of the nutrient and limits the growth of the cells outside the desired region. Often time-release nutrient matrices are used within the desired region of survival.

However, there are some problems inherent in the foregoing approaches. For example, the depletion of the nutrient will eventually cause the cells to die, the local environment may be contaminated by leaching of the nutrient or its byproducts, or a nutrient gradient may be formed that forces a selective pressure on the cells leading to the evolutionary transformation of the cells from auxotrophs to prototrophs, allowing their escape into the environment.

Another method of containment for auxotrophic cells physically contains them within a barrier, such as a membrane or matrix having pore sizes smaller than the cells. Limitations of this approach include the reduced ability of material to flow to and from the cells due to physical properties of the barrier, and the potential of the barrier to breach and release the cells contained within.

Despite the foregoing, there continues to be a need for improved methods for limiting the escape potential of cells and that can provide a high level of survival for the cells within a limited area and also reduce the environmental impact of maintaining the organism, as well as reduce the escape potential of the organism. The introduction of an exogenous substrate immobilized compartmentalized component to the cell is therefore a preferred embodiment of the present invention that ensures cellular survival and minimal environmental impact, yet prevents transfer of the component from the compartment by restricting the component’s ability to interact with cellular chromosomes and other large cellular macromolecules. Thus the cell is transiently transformed from an auxotroph to a substrate-dependent prototroph. Growth off the substrate will result in cell death, and daughter cells are not able to inherit the component due to the compartmentalization.

In accordance with a first aspect, one exemplary embodiment of the disclosure provides a method for the transient transformation of at least one living biological cell having an intact cell membrane defining an intracellular domain. The method includes introducing at least one compartmentalized exogenous component to the intracellular domain of the cell, wherein the component is fixed within a recessed compartment at a tip of a cellular penetrant structure being dimensioned to extend through the cell membrane into the intracellular domain without significantly damaging the cell, and wherein the cell is penetrated by at least a portion of the tip of the penetrant, and wherein the component is retained within the compartment and wherein the compartment is dimensioned to restrict interaction of the component with cellular macromolecules.

In accordance with a second aspect, the disclosure provides an apparatus for the transient transformation of at least one living biological cell having an intact cell membrane defining an intracellular domain. The apparatus includes an immobilized cellular penetrant structure having a tip with a recessed compartment dimensioned to extend through the cell membrane without significantly damaging the cell, and at least one extracellular component fixedly attached to at least a portion of the surface of the recessed compartment.

An advantage of the disclosed embodiments is the transient introduction of a compartmentalized exogenous component fixedly attached within the tip of a cellular penetrant structure to the intracellular domain of the cell. The component transforms the cell, but only while the penetrant structure remains within the dependent cell. Cell growth off the penetrant structure would result in cell death. The immobilization of the essential component within a compartment enables functional activity of the component within the cell but does not allow the component to be passed from one cell to another or to be inherited by daughter cells. The compartmentalization of this component prevents the transfer of the component from the compartment and into the host cell by restricting the access of the component to other large cellular macromolecules such as chromatin or replication holoenzymes. The compartmentalization can also act to protect the component from degradation by cellular enzymes, thus providing for longer activity of the delivered component.

The exogenous component may be a gene or set of genes that encode a specific enzyme or set of enzymes required by the cell either to synthesize a required nutrient or to degrade a toxic agent. The component may be the required enzyme or set of enzymes itself, fixedly attached in a manner that allows catalytic functionality within the cell. The component may also be another molecule or set of molecules that influences or assists in the required reactions within the cell. The component may also be a combination of at least one gene and at least one enzyme required for posttranscriptional modification of the gene message, each subcomponent attached fixedly to a surface of the recessed compartment of the cellular penetrant substrate.

A further advantage of the disclosed embodiments is due to the attachment of the enzyme, DNA, or nutrient component within a recessed compartment at the tip of an immobile cellular penetrant structure on a substrate. By such attachment the cells or organisms can be forced to reside only on the substrate while being mounted on the penetrant structure and the component is prevented from any inheritable incorporation into the cell. Immobilization of the cells on the cellular penetrant substrate limits the potential of the cells to escape from the substrate.

BRIEF DESCRIPTION OF THE DRAWINGS

The present invention can best be understood by reference to the following detailed description of exemplary embodiments when considered with the attached drawings, not to scale, in which:

FIG. 7*a* is a diagrammatic illustration of a fabricated cell penetrant structure having a silica sheath, a carbon core, and a recessed compartment.

FIG. 7*b* is a diagrammatic illustration of the structure of 7*a* additionally having a fragment of DNA covalently condensed to the carbon core.

FIG. 7*c* is the diagrammatic illustration of 7*b* additionally having a coating of a blocking agent.

FIG. 7*d* is the diagrammatic illustration of 7*c* with the blocking agent partially removed from the silica sheath tip of the structure.

FIG. 7*e* is the diagrammatic illustration of 7*d* with the silica sheath tip functionalized with organosilane.

FIG. 7*f* is the diagrammatic illustration of 7*e* with the organosilane functionalized by the condensation of the enzyme poly-A-polymerase.

FIG. 7*g* is the diagrammatic illustration of 7*f* with the remainder of the blocking agent dissolved.

DESCRIPTION OF THE EXEMPLARY EMBODIMENTS

Figure 1:
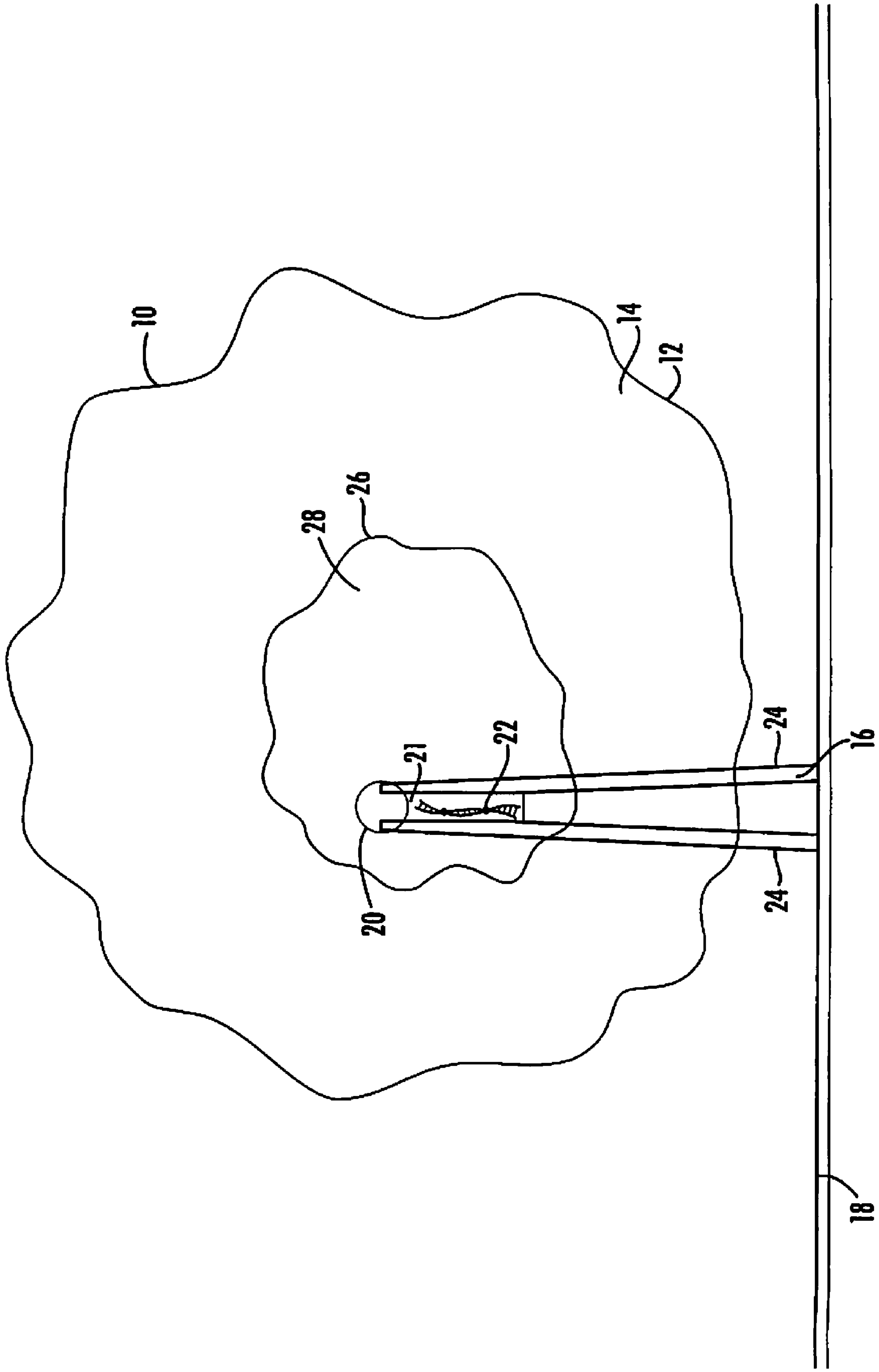
FIG. 1 is a diagrammatic illustration of a cell being penetrated by a structure that delivers a component to the cell, the structure extending from a substrate through a cell membrane and nuclear membrane into the cellular nucleus.
Figure 2:
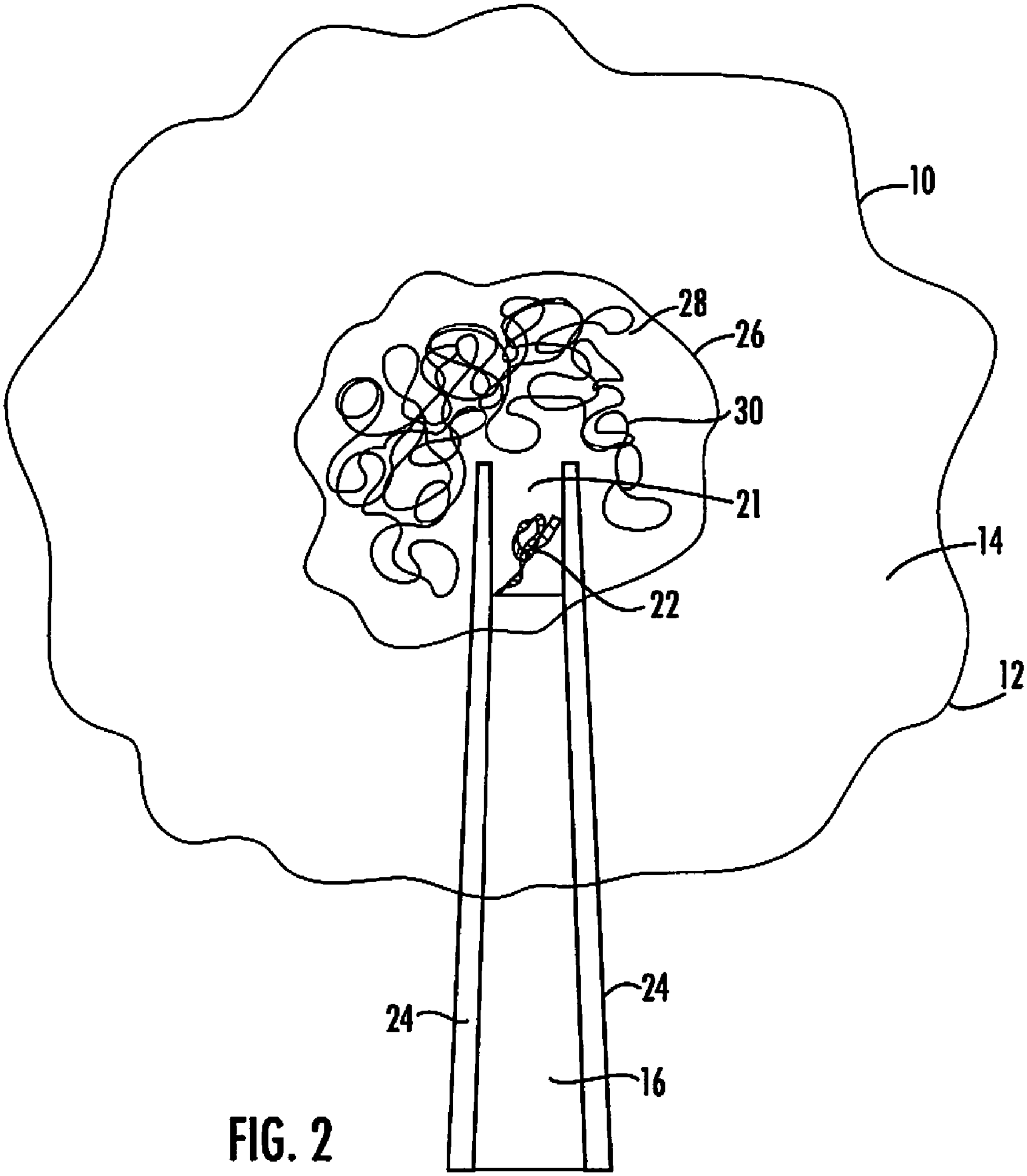
FIG. 2 is a diagrammatic illustration of a cell having an intact cell membrane and an intracellular domain being penetrated by a cell penetrant structure having a tip with a recessed compartment enclosing a fixedly attached component, wherein the structure is coated by a sheath and extends through the nuclear membrane into the cell nucleus where the component is activated yet sequestered from interaction with a cellular chromosome.

According to one exemplary embodiment of the disclosure, an apparatus capable of the transient transformation at least one biological cell having an intact cellular membrane defining an intracellular domain is described, as illustrated in FIGS. 1 and 2. The apparatus includes an immobilized cell penetrant structure 16 grown on a substrate 18 and having a tip 20 providing a recessed compartment 21 dimensioned to extend through the cell membrane 12 into the intracellular domain 14 and through the nuclear membrane 26 into the cellular nucleus 28 without significantly damaging the cell 10, and an extracellular component 22 fixedly attached to at least a portion of a surface of the recessed compartment 21 of the structure 16. The structure is coated by a sheath 24. The method and apparatus enable the cell 10 to express the component while the penetrant structure 16 remains within the dependent cell 10. Removal of the penetrant structure 16 from the cell 10 will result in a cessation of component expression by the cell. FIG. 2 additionally illustrates how the component 22 fixedly attached within the compartment 21 is restricted from interaction with the chromatin 30 of the cell 10.

The cellular penetrant may be any structure capable of delivering a compartmentalized component to the cell by penetrating the intracellular domain without killing the cell. Ideally, but not required, the cellular penetrant is immobilized to a substrate so that the survival of the penetrated cell is limited to the substrate. Also, many penetrant structures may be configured to exist on a single substrate as an array, so that many cells may be maintained at one time on the penetrant structures on the substrate. The components fixedly attached within the recessed compartments of the penetrant structures may be identical or different to allow different organisms or organisms with different functions to coexist on the same substrate. Also, more than one component may be configured upon a single penetrant structure.

Particularly suitable cellular penetrants for the methods and apparatus described herein are carbon partial nanopipes formed from carbon nanofibers, due to their physical and chemical characteristics. Other cell penetrant structures such as micropipettes, pulled capillary tubes, optical fibers, silicon carbide whiskers, silicon nitride whiskers, and silicon needles have all been used for the delivery of material to the intracellular domain of a cell. However, slow throughput, random delivery, the possibility of genetic recombination of the component with the target cells, or the inability to immobilize the target cells may prevent these methods from being used on a large scale.

Carbon partial nanopipes grown on a substrate are able to substantially overcome the limitations of the other cellular penetrants described above. Carbon partial nanopipes also fulfill a requirement that the penetrant structure be able to penetrate into a live cell yet allow cell viability to be maintained. An embodiment of the penetrant structure may also be an array of carbon partial nanopipes grown on the substrate and aligned in a substantially orthogonal orientation to the substrate.

Figure 3:
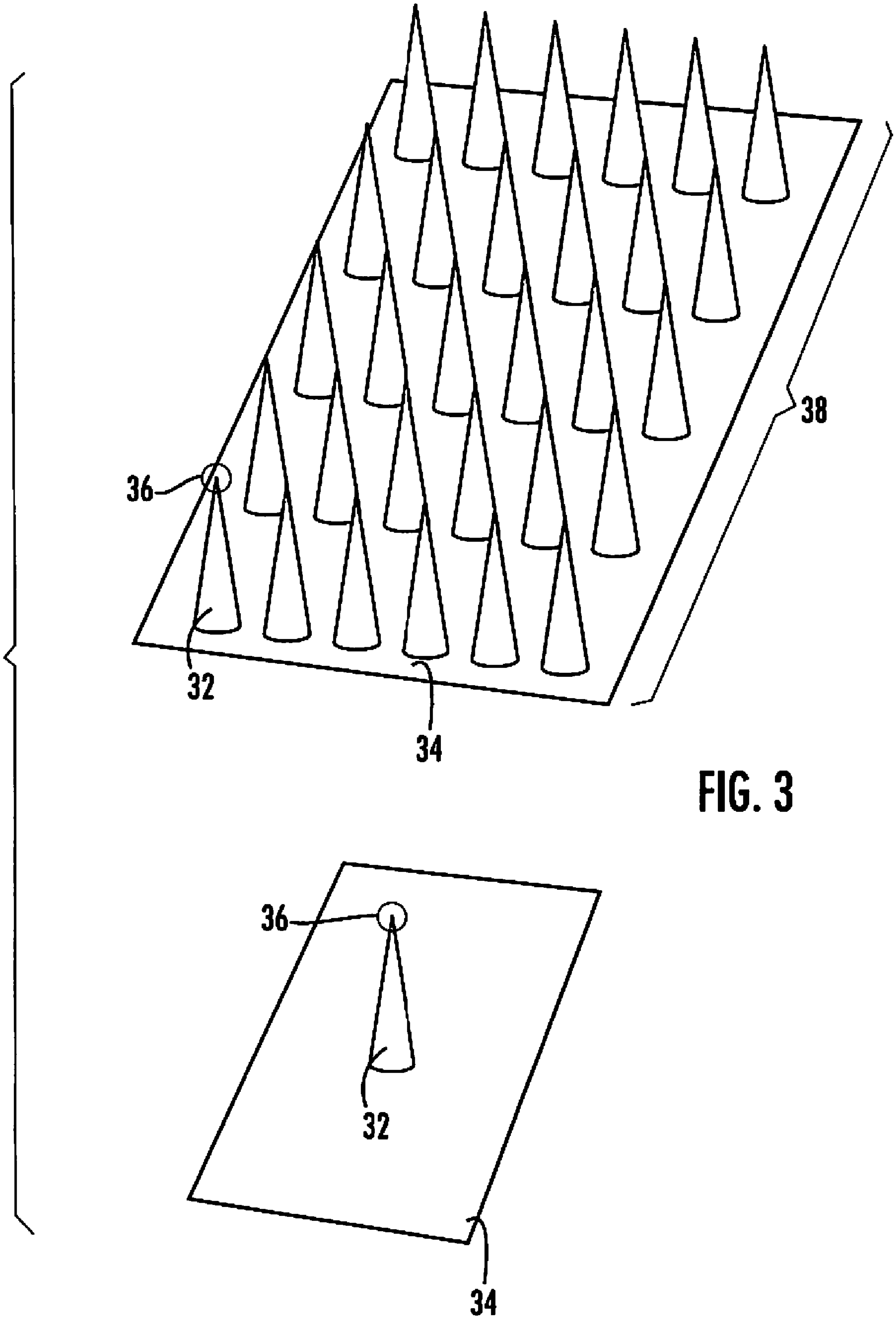
FIG. 3 is a diagrammatic illustration of a carbon nanofiber on a substrate having a tip, and an array of carbon nanofibers on a substrate, each nanofiber having a tip.

Accordingly, the disclosure provides a cell penetrant structure provided by a carbon partial nanopipe or an array of carbon partial nanopipes formed from a carbon nanofiber 32 or an array 38 of carbon nanofibers 32, each nanofiber having a tip 36 and grown in a substantially orthogonal orientation on a substrate 34 so as to be vertically aligned, as shown in FIG. 3. This structure is referred to herein as a vertically aligned array of carbon nanofibers ("VACNF"). Carbon partial nanopipes formed from carbon nanofibers, as described herein, are ideally dimensioned to penetrate cellular membranes without significantly damaging the cell, and the growth of the nanofibers on a substrate ensures immobilization of the nanofibers.

The parameters of the carbon partial nanopipes formed from carbon nanofibers, including the size, shape, location, orientation, and chemical composition of both the fiber core and the fiber sheathing, may be finely controlled during a plasma enhanced chemical vapor deposition ("PECVD") growth process, resulting in structures that can vary in physiochemical properties depending on the type of biological cell they are used to penetrate. In one embodiment, the carbon nanofibers may be catalytically synthesized in a dc-PECVD process that uses standard 3" or 4" silicon or fused silica wafers as the nanofiber growth substrate.

The sites of nanofiber growth on the substrate are defined by photolithography and the deposition of a thin film of metal dots as a catalyst. Typically the catalytic metal is nickel, and the film is from about 50 Å to about 1000 Å thick. However, other metals such as iron, cobalt, and alloys thereof may be used. After fabrication of the nanofibers, the catalyst particle(s) may be removed from the substrate by chemical etching (e.g., nitric acid) and/or plasma etching. When the substrate is heated to about 700° C. and dc plasma is initiated, the thin film dots nucleate into isolated nanoparticles that will each initiate the growth of a single nanofiber. A buffering layer between the nickel layer and the substrate may be employed to aid in the nickel nucleation, the buffer comprising titanium dioxide or silicon dioxide.

According to one embodiment, a suitable substrate with the patterned catalyst particle array thereon is the placed onto the cathode of a glow discharge PECVD chamber and heated to approximately 700° C. in a flow of acetylene and ammonia gasses. After formation of the plasma, carbon nanofibers grow from the defined catalyst particles in the patterned array. Carbonaceous species decompose at the surface of and diffuse through the catalyst particle and are deposited into a growing nanofiber between the catalyst particle and the substrate. Such nanofibers, with the catalyst at the tip, grow in a substantially orthogonal orientation to the substrate due to the presence of an electric field. The diameter of the nanofibers may be manipulated by the size of the catalytic particles, and the nanofibers length can be controlled by the amount of time the plasma is being generated. The overall shape of the nanofibers may be made more conical or more cylindrical by altering the proportions of the gasses in the gas composition within the chamber.

An important aspect of nanofiber synthesis with respect to biological applications is that in addition to depositing carbon nanofibers on the substrate using the metal catalyst particles, species generated in the plasma also deposit as a film on the sheath and tip of the nanofiber and, to a lesser extent, on interfiber surfaces between nanofibers. An ammonia etch gas is employed throughout the growth process to continuously remove the film from the fiber tip as the film will passivate the catalytic activity of the metal catalyst particles and terminate fiber growth.

Variation of synthesis parameters, particularly the acetylene/ammonia ratio, enables selection of the amount of film allowed to remain on the nanofiber sheath as a covering of the highly ordered carbon core. The chemical composition of this film may be tailored from essentially pure carbon to carbon heavily doped with nitrogen as well as substrate materials. The composition of fiber sheathing affects surface adsorption and other physicochemical phenomena. For example, forests of carbon rich fibers exhibit some hydrophobicity immediately following growth while nitrogenated films exhibit reduced hydrophobicity with increasing nitrogen content. Increased nitrogen content also reduces the electrochemical activity of the surface.

The composition of the sheath also allows for the carbon core to be partially removed by etching, leaving the sheath intact so that a recessed compartment is formed at the tip of the nanofiber so as to form a partial nanopipe.

Figure 4:
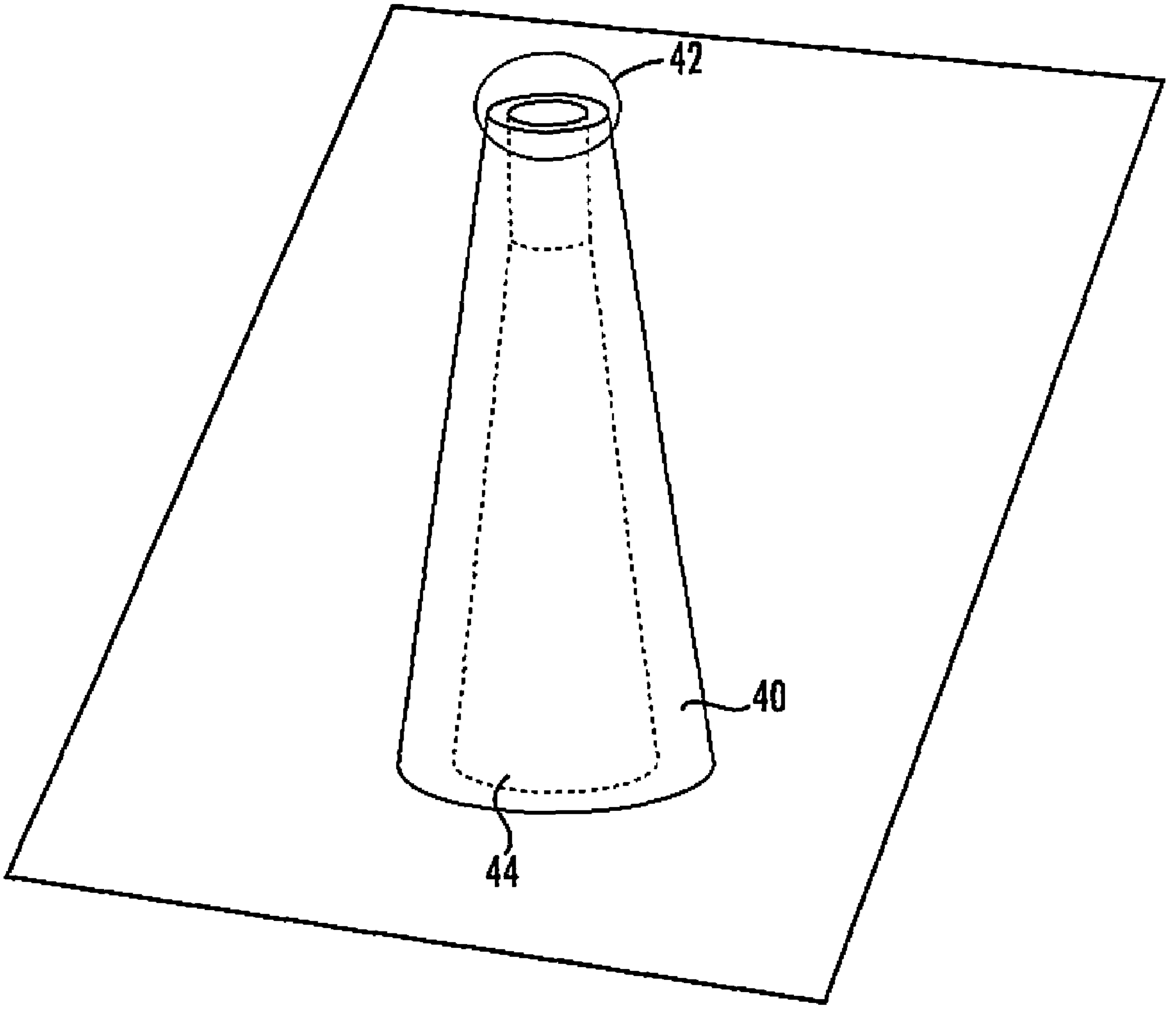
FIG. 4 is a diagrammatic illustration of sheathed carbon partial nanopipes having tips with recessed compartments formed by the partial etching of the enclosed carbon cores.

Nanofibers may be partially piped by a variety of methods. In the simplest form, a nanofiber catalytically tip grown using a metal catalyst particle may be partially piped by removing the catalyst particle at the tip. For example, a nanofiber synthesized using PECVD will host a nickel particle at its tip. This nickel particle can be removed by first removing a cap layer of carbon covering the nickel particle using an oxygen plasma reactive ion etch. The nickel may then be dissolved with a variety of methods, including etching in nitric acid, acetic acid, or 0.1M MES buffer at pH 4.5. The result is a nanofiber with a recessed cavity where the nickel particle once resided at the tip of the structure. Heterogeneous nanofibers may also be partially piped. For example, nanofibers that have been coated with sputtered metals from the substrate during growth can be oxygen plasma etched to remove part or all of the carbon core, provided the oxygen etch does not etch the sheathing material of the nanofiber. For example, $Si_xN_y$ coated nanofibers may be oxygen plasma etched to remove the internal carbon core, leaving behind a partial pipe comprised of a $Si_xN_y$ sheath. FIG. 4 shows such a partially piped nanofiber sheath 40 having a tip 42 with an etched carbon core 44.

Nanofibers may also be coated with other materials and then etched to remove at least a part of the carbon core. For example, fibers may be coated with PECVD oxide, and subsequently the oxide at the tip may be removed with an anisotropic silicon dioxide reactive ion etch. Following emancipation of the VACNF at the tip, the nickel particle may be removed as indicated above. Then the carbon core can be removed using an oxygen reactive ion etch. Alternatively, the carbon core can be removed by thermal treatment (heating in an oxygen containing environment to lose C in the form of CO2) or, if the carbon core is electrically addressable, by electrochemical oxidation, for example by applying 1.8V vs AgCl (3M KCl) to the carbon core in a 1N solution of NaOH.

One embodiment of the cellular component that is attached to a surface of the recessed compartment of the foregoing penetrant structure may be a section of DNA that codes for one or more gene products which catalyze a reaction or series of reactions necessary for the survival of the cell. The DNA section may be linear or a closed circular DNA plasmid.

Another embodiment of the cellular component that is attached to the foregoing penetrant structure may be an enzyme or complex of enzymes that catalyze a reaction or series of reactions necessary for the survival of the cell. The enzyme may be a polypeptide or an RNA enzyme.

Another embodiment of the cellular component includes both a gene and an enzyme, such as a poly-A polymerase, functioning to modify the transcriptional product of that gene, each fixedly attached to a different region of the compartment. For example, the gene could be attached to the carbon core within the recessed compartment while the enzyme could be attached to the sheathing material at the mouth of the compartment.

In the disclosed embodiments, the reaction or series of reactions necessary for the survival of the cell may be anabolic, wherein the reaction is to synthesize a vital compound required by the cell, or catabolic, wherein the reaction is to degrade a toxic or a potentially toxic compound. Choice of the component and the reaction must be complementary to one another and will vary depending on the organism or cell lineage used.

In the disclosed embodiments, the component is tethered, or otherwise constrained or immobilized within a recessed compartment within the penetrant structure such that the component is accessible and functional within the cell, but is not removable from the recessed compartment of the penetrant structure and is prevented from interacting with any large cellular macromolecules such as cellular chromatin. As such, a cell that requires the component for survival can only survive if access to the component is maintained, i.e. the recessed compartment of the penetrant structure and attached component therein remain within the cell.

Figure 5:
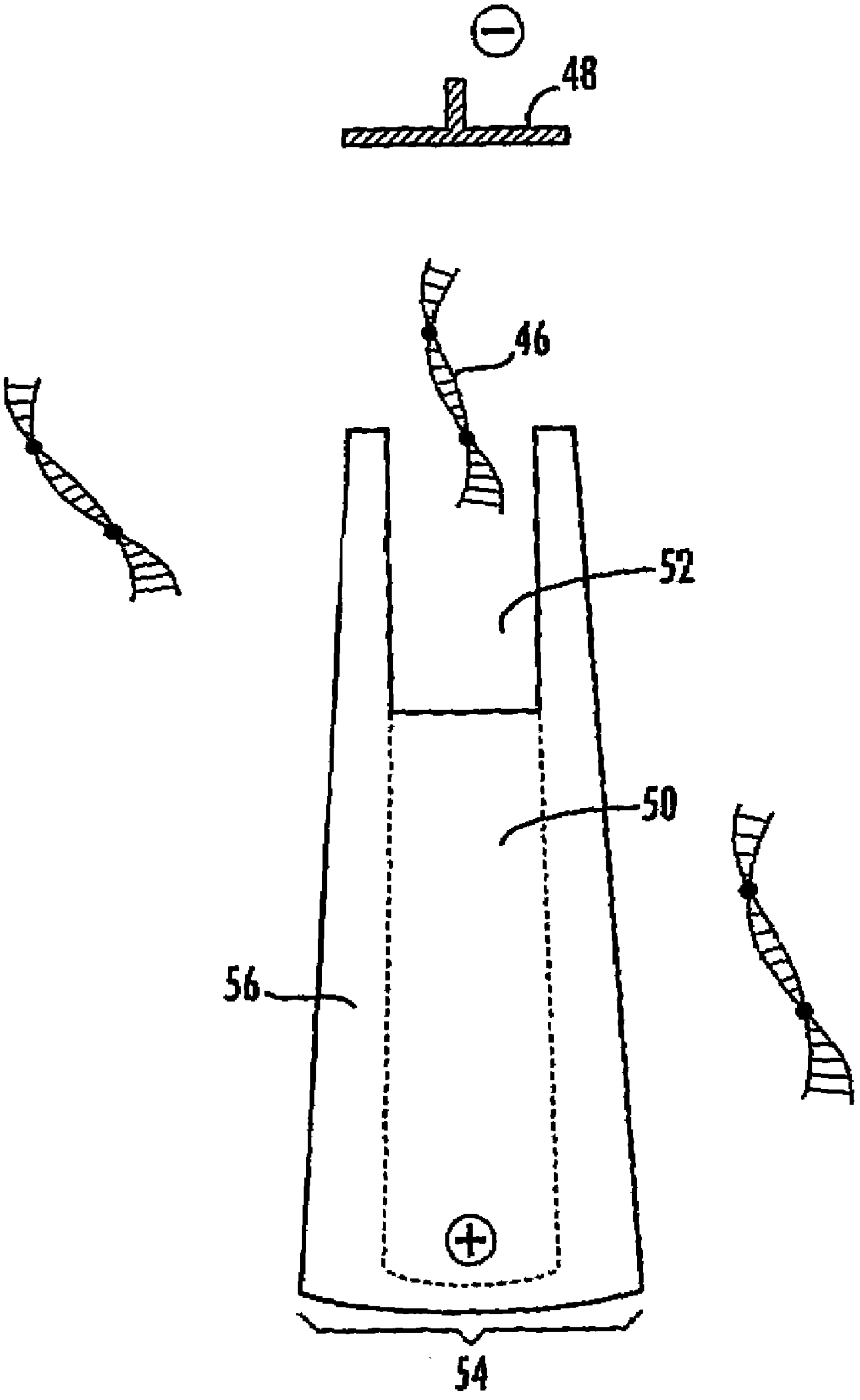
FIG. 5 is a diagrammatic illustration showing propidium iodide labeled DNA migrating from a platinum electrode to the electrically addressable carbon core of the partial nanopipe and into the recessed cavity of a partial carbon nanopipe having a sheath and grown on a silicon substrate.

Molecules may be loaded into the recessed cavity of partial nanopipes using a variety of techniques. Passive diffusion can be used to accumulate molecules within a partial pipe by immersing the partial pipe in a solution containing the molecule to be loaded into the pipe. If trapped gases are within the recessed cavity of the partial pipe, they must be dissolved prior to solution based materials entering the partial pipe. If the core of the nanopipe is a conductive material and the sheath of the nanopipe is an insulator and the core is electrically addressable, the core may be used as one terminal of a circuit for electrokinetic loading of the nanopipe, such as by electrophoresis and/or electroosmotic flow. For example, for a nanopipe constructed from a VACNF template, a residual carbon core remains in the nanopipe interior. Electrical connection to this carbon core enables the use of the carbon as a terminal for electrokinetic loading of the nanopipe. For example, by applying positive potentials with respect to another electrode within the solution in which the nanopipe structure is immersed, negatively charged species may be electrophoretically loaded into the nanopipe. FIG. 5 demonstrates the loading of the recessed compartment 52 of a partial carbon nanopipe 54 with propidium iodide labeled DNA 46 by application of an electrophoretic potential of +500 mV between the carbon core 50 of an electrically addressable partial nanopipe 54 having a sheath 56, and a platinum electrode 48 within a solution of propidium iodide labeled plasmid DNA 46.

As described in more detail below, the component may be immobilized within the recessed compartment on the penetrant structure by fixedly attaching the required cellular component to a surface of the recessed compartment of the cellular penetrant structure. Immobilization of the component may be accomplished by either a covalent bond or a noncovalent interaction between the component and the surface. Additionally, a linking molecule or a series of linking molecules may be similarly attached between the component and the surface to impart a higher range of mobility to the component without allowing it to become released from the compartment while inside the cell. A further embodiment constrains the component by the polymerization of monomers onto the opening of the compartment creating a scaffold or cage for entrapping and immobilizing the component within the compartment. Another embodiment entraps the component within the compartment with a semipermeable membrane covering the opening of the compartment.

To maintain their position within the recessed compartment of the penetrant structure, components may either be retained behind a membrane material at or near the cavity mouth, or they may be immobilized by chemical attachment to surfaces within the recessed cavity. The recessed compartment of the penetrant structure, in these embodiments, has an internal diameter of about 50 nm and an outer diameter of about 100 nm, but other sizes may be appropriate in other applications. By limiting the entrance diameter, or by sealing the entrance with semipermeable membrane materials, molecules may be retained, or elsewise immobilized within the recessed compartment, but remain accessible by and functional with smaller molecules within the cell, such as RNA polymerases which have a width of about 10 nm to 20 nm. Even though the width of a DNA double helix is only about 2 nm, chromosomal DNA can vary in length from micrometers to centimeters or more, and thus would be hindered from interaction with the contents of the localized compartmental environment.

One preferred embodiment of the present disclosure is to covalently tether the molecule to be immobilized within the recessed cavity of the penetrant structure, as described in more detail below. For example, most polypeptides can be covalently tethered to another molecule by chemically linking to the C—or N—(carboxy or amine) terminus of the polypeptide, or to specific moieties on individual peptides. Other complexing strategies are also possible, including cross linking of cysteine residues, hex-his tagging of polypeptides and chelation to metals or complexed metals on substrates.

Electrostatic interactions are also possible for immobilization strategies. Other strong interactions may also be employed such as avidin-biotin or strepavidin-biotin interactions. Gold-thiol interactions are useful for the immobilization of thiolized molecules. The interaction of carboxylic acids with nickel oxide is useful for the immobilization of biological species that feature one or many carboxylic acid groups.

In addition to direct immobilization within the penetrant structure, intermediate materials may also be employed. For example, linkage groups may be employed using the same or other tethering strategies, provided that ultimately the molecule to be immobilized is immobilized within the recessed cavity of the penetrant structure or linkage groups within the cavity of this structure. Adding linkage groups between the penetrant structure and the molecule can increase activity of the molecule, or can increase the ability of the cell to use the molecule by providing improved access of interacting molecules within the cell by reducing the steric hindrance imposed on the component by the penetrant structure.

Partially piped carbon nanofibers are a preferred embodiment of a suitable penetrant structure capable of covalent bonding with a desired component because they are often richly populated with defect sites and functional handles that enable post-synthesis chemical modification of the nanofiber surfaces. The functional handles on the carbon nanofibers include carboxylic acids, hydroxyls, carbonyls, and quinones. A variety of macromolecules, for example plasmid DNA or the enzyme soybean peroxidase, may be covalently attached to such moieties on the surface of carbon nanofibers and at least some of these immobilized components retain their transcriptional or enzymatic activity.

For example, to allow covalent attachment of macromolecules bearing primary amine sites, carbon regions within recessed compartments of nanopipes may be etched for 5 min in an RF oxygen plasma to increase the coverage of oxygen-containing moieties, including carboxylic acid groups, on the carbon surface. The nanopipes are then submersed in 0.1M 2-(N-morpholino) ethane sulfonic acid ("MES") buffer at a pH of 4.5 containing 10 mg/mL of 1-ethyl-3-(3-dimethylaminopropyl)carbodiimide ("EDC") and the macromolecule to be immobilized, as demonstrated by Cai et al., (2003 Anal. Bioanl. Chem. 3752:289). The reaction mixture is agitated on an orbital shaker for two hours at room temperature to condense primary amines found on macromolecules to the carboxylic acid sites of oxygen plasma etched carbon surfaces within the recessed compartments of the nanopipes.

Following the condensation reaction, the nanopipe arrays may be rinsed extensively in phosphate buffered saline with high salt (500 mM NaCl) and water to remove nonspecifically adsorbed macromolecules. Using this approach, DNA has been immobilized within the recessed compartment of partially piped silica-coated VACNFs and visualized with propidium iodide and fluorescent microscopy.

Penetrant structures, including nanofiber surfaces, may be physically coated with nanometer thicknesses of other materials, including metals, silicon nitride, and silicon dioxide. These surfaces may subsequently be modified, such as using organosilane reactions to derivitize a silicon dioxide coated surface. Gold metallization may be used for thiol-chemistry immobilization. The nickel catalyst particles at the tips of nanofibers may be used to capture carboxylic acid bearing molecules or following chelation for capturing histidine-tagged species, thereby providing material capture at only the tip of the nanofiber.

Figure 6:
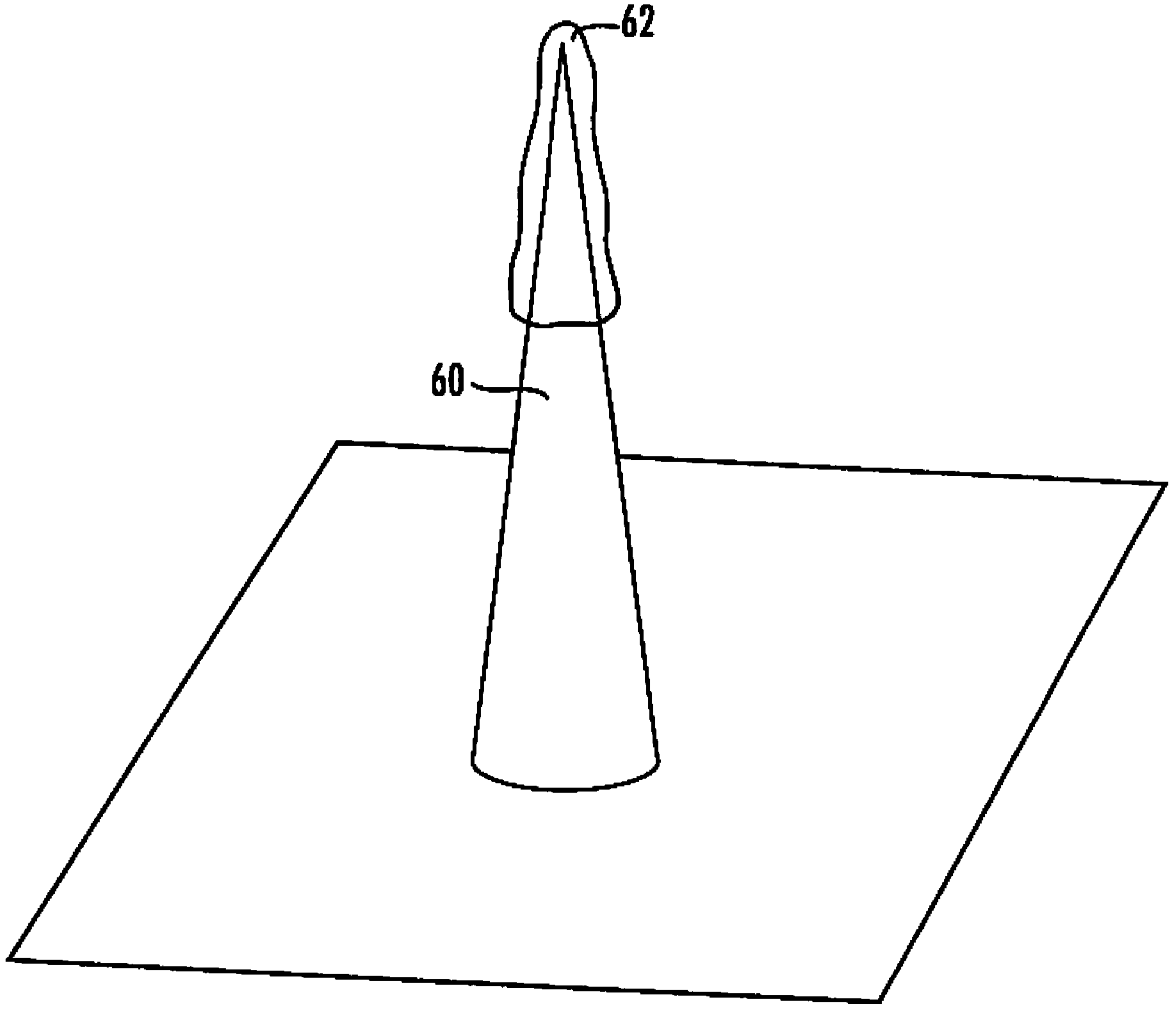
FIG. 6 is diagrammatic illustration of a carbon nanofiber having a sheath of polypyrrole polymerized thereon.
Figure 7G:
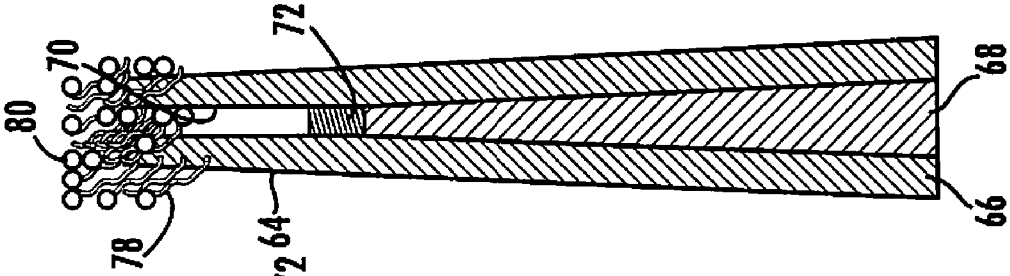
FIGS. 7*a*-7*g* are a series of diagrammatic illustrations depicting the process of immobilizing two different species of components to two different localities on the cell penetrant structure.
Figure 7F:
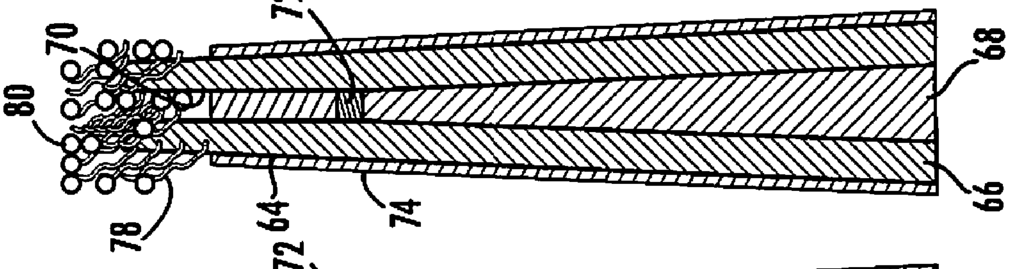
Figure 7E:
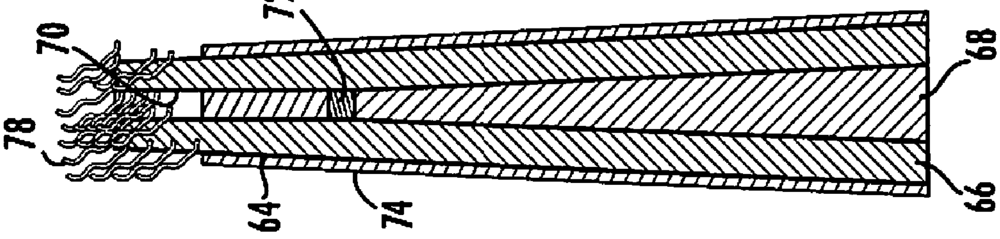
Figure 7D:
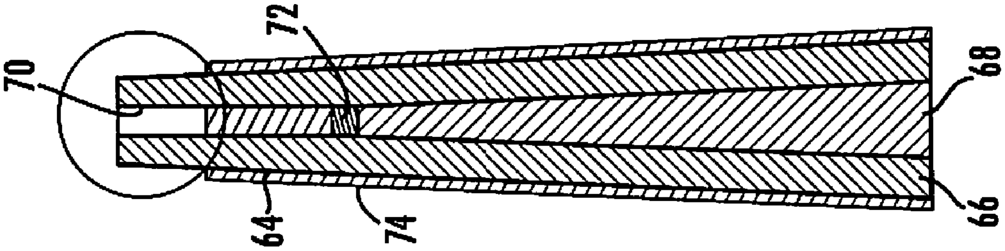
Figure 7C:
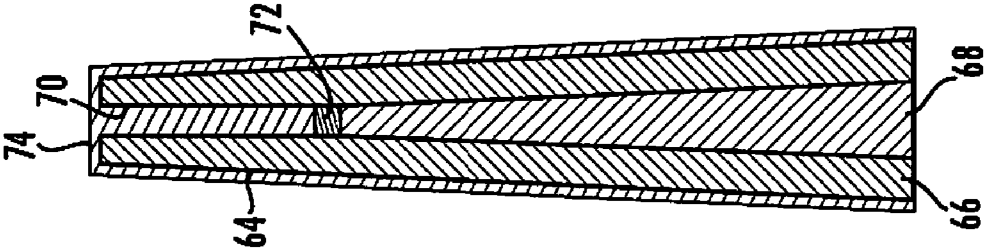
Figure 7B:
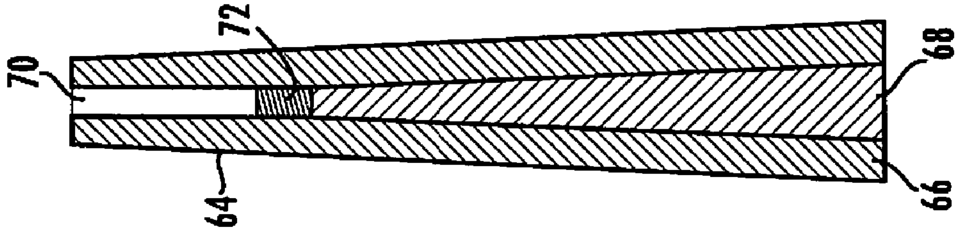
Figure 7A:
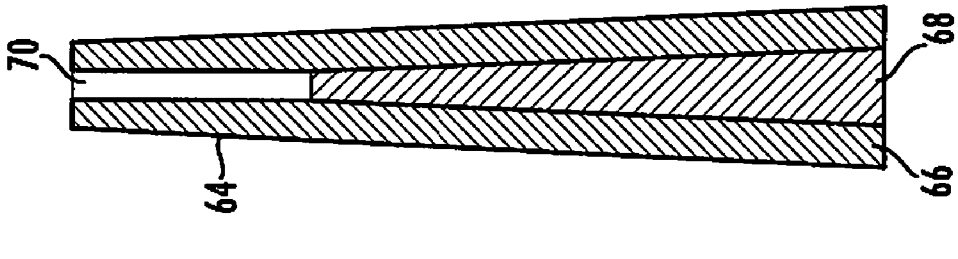

For metallic or semimetallic penetrant structures, including VACNFs, electrochemical strategies provide additional derivitization schemes. A metal selected from gold, silver, nickel and platinum may be electrodeposited onto penetrant structure surfaces both as discrete nucleated islands and as continuous films. The foregoing procedure may be used to provide metal interaction sites for a variety of binding chemistries (i.e. thiol/gold and carboxylic acid/nickel). Electrically addressable penetrant structures, including nanofibers, may be used as scaffolds for electropolymerization of electrically conductive polymers, such as polypyrrole. The electroanalytical techniques used for these depositions allow very well-defined layers of polypyrrole to be formed, and anionic species can be incorporated to the polypyrrole matrix as it forms. Such techniques have been used for immobilization of enzymes which still can retain some of their activity for enzyme-mediated redox reactions on the carbon electrode, and therefore they can likely be used to immobilize molecules that are required for the survival of cells. Similarly, polymerization of monomers onto a penetrant structure may also be used to immobilize via entrapment necessary molecular species onto a penetrant structure. FIG. 6 illustrates a carbon nanofiber 60 having polypyrrole 62 polymerized thereon.

In a further embodiment, intermediate materials may also be used in addition to direct immobilization of components onto the penetrant structure. For example, linkage groups may be used using the same or different tethering strategies, provided that the component to be immobilized is immobilized to the penetrant structure or linkage groups on the structure. Adding linkage groups between the penetrant structure and the component can increase activity of the component, or can increase the ability of the cell to use the component by providing improved access of interacting components within the cell (i.e., reduced steric hindrance imposed by the penetrant structure).

In the preferred embodiment of the present disclosure, the penetrant structure features a unique material within the recessed compartment of the structure such that this area may be exclusively derivitized with a molecule or molecules without derivitizing the exterior surface of the penetrant structure. This provides a method of immobilizing a desired component only within the recessed cavity of the structure and not immobilizing that component on any other surface if the structure.

A preferred embodiment is a partial nanopipe constructed of a dielectric sheathing material (SiO2) or ($Si_xN_y$) containing a carbon nanofiber core at the bottom of the recessed compartment. Here, the carbon surface within the recessed compartment can be derivitized with aforementioned techniques (i.e. EDC mediated amidization) without derivitizing any part of the sheathing structure.

If desired, however, the sheathing material may in turn be derivitized. This may prove advantageous for example to further limit the ability of species to enter into the recessed environment. It may also provide for the ability to modify species as they enter or leave the confines of the recessed compartment. In one embodiment, an mRNA transcript from immobilized DNA within the pipe may be post-transcriptionally modified by an enzyme tethered to the internal surface of the pipe sheath (for example, an enzyme related to polyadenylation, end-splicing, or intron-splicing of mRNA). For example, organosilane reactions can be used to generate carboxylic acid sites on the silica sheath. An enzyme such as poly-a-polymerase could then be attached by an EDC condensation reaction as described previously. In this manner, more than one exogenous component could be affixed to the penetrant structure.

FIG. 7 is a drawing depicting the multi-step process of adding more than one type of covalently tethered component to the penetrant structure. A fabricated cell penetrant structure 64 having a silica sheath 66, a carbon core 68, and a recessed compartment 70 has a fragment of DNA 74 covalently condensed by an EDC condensation reaction to the carbon core 68. The entire structure 64 is then coated with a thin film of a blocking agent 74, such as photoresist. The blocking agent 74 is then partially removed from the silica sheath tip 76 of the structure 64. The silica sheath tip is then functionalized with organosilane 78. The organosilane 78 is then functionalized by the EDC condensation of the enzyme poly-A-polymerase 80. The remainder of the blocking agent 74 is then dissolved, completing the fabrication of a partial carbon nanopipe having more than one type of functional component.

A variety of substrates may be used for growing the penetrant structures described herein. Suitable substrates include, but are not limited to, silicon or fused silica wafers. A particularly suitable substrate is a silicon wafer.

In order to further illustrate aspects of the disclosed embodiments, the following non-limiting examples are given.

EXAMPLE 1

A preferred embodiment to limit interaction of introduced components and cell materials is to covalently tether the components within the recessed compartment of the penetrant structure such that they are not free to leave the confines of the recessed compartment and yet maintain activity. VACNFs, the precursors and active elements of a VACNF based nanopipe, have been used to demonstrate the covalently tethered DNA may be attached to penetrant structures, penetrated into cells, and used by the intracellular machinery to synthesize a gene product off the tethered plasmid. Deterministically synthesized VACNFs were modified with covalently-linked plasmid DNA and were subsequently inserted into cells. In these experiments, the expression of a reporter gene, green fluorescent protein ("GFP"), was used to indicate successful intracellular integration and delivery of plasmid DNA by the fiber and to provide a marker for continued viability of the interfaced cell. VACNF chips were prepared with plasmid DNA covalently linked to the VACNFs such that there would be no free plasmid available for segregation to progeny. Centrifugation and press integration methods were used to impale cells onto the VACNF chips with plasmids covalently bound to the VACNFs using an EDC-condensation reaction and four control chips that had been incubated with the DNA reaction mixture, but without the EDC. Both sample types were extensively rinsed following the incubation step. For the control samples, without EDC in the reaction mix, there should be no covalent binding of DNA to the nanofiber scaffold and subsequent extensive rinsing would remove non-specifically bound DNA from the nanofibers. Following centrifugation and pressing of cells onto these fibered chips, the covalently-linked samples resulted in 81, 198, 65, and 102 GFP+ cells on each chip, respectively. The control samples resulted in no transfected GFP+ cells on three chips and one faint GFP+ cell on the fourth chip, indicating that non-specifically adsorbed plasmid DNA had effectively been removed from the samples during rinse steps. Unlike previous experiments with samples non-covalently spotted with plasmid, no off-chip GFP+ cells were observed, indicating that GFP expression required the continued retention of the DNA-derivitized VACNF element within the cell.

EXAMPLE 2

Experiments demonstrating the continued viability of nanofiber penetrated cells were conducted to show that DNA could be delivered and expressed by the penetration of nanofibers into viable cells. The fibers synthesized for these experiments were grown from 500 nm diameter nickel catalyst dots that were photolithographically defined at 5 g/m intervals on 100 mm, n-type silicon wafers. Plasma conditions were selected to provide conically-shaped fibers of 6-10 μm length (depending upon growth time) with tip diameters of 20-50 nm and base diameters of approximately 1 μm. Following nanofiber growth, the wafers were cleaved into 3 mm×3 mm chips that were covered with VACNF arrays with a 5-μm pitch. The nanofiber arrays were surface-modified with plasmid DNA. The plasmid used in these experiments was pGreenLantern-1 which contains an enhanced green fluorescent protein ("eGFP") gene with the CMV immediate early enhancer/promoter and SV40 t-intron and polyadenylation signal, and no mammalian origin of replication. Plasmid DNA at various concentrations (5-500 ng/μl) was spotted onto the chips as 0.5-1 μl aliquots and allowed to dry. The cell line used predominantly for these experiments was a subclone of the Chinese hamster ovary ("CHO") designated K1-BH4.

Cells were routinely grown in Ham's F-12 nutrient mixture supplemented with 5% fetal bovine serum and 1 mM l-glutamine. Cell cultures were grown in T-75 flasks and passaged at 80% confluency by trypsinization using trypsin-EDTA. In preparation for fiber mediated plasmid delivery, adherent cells were trypsinized from T-75 flasks, quenched with 10 ml of Ham's F-12 media, pelleted at 100 G for 10 min, resuspended in phosphate buffered saline ("PBS"), counted, and diluted in PBS to a desired density ranging from 50,000 to 600,000 cells/ml.

The cells were integrated with DNA modified VACNF arrays by centrifuging them out of suspension onto the fiber array. CHO cells are spheres approximately 7 μm in diameter while in suspension. As such, nanofiber arrays were synthesized at a pitch of 5 μm, such that, during centrifugation a cell would likely interact directly with only a few nanofibers. Following a culture period of at least 24 hours, the interaction of plasmid spotted nanofibers and cells was evaluated by observing plasmid-coded GFP expression with fluorescence microscopy. Using only centrifugation onto the array at 600 G, GFP expression was typically detected in cells at only a very low frequency (<1% of the cells on the fibered substrate). Using a moderate pelleting force (600 G) to position cells upon the nanofiber array, and then including a subsequent press step typically increased the number of GFP+ cells, often by as much as a factor of 5 and occasionally even more significantly, with some tests resulting in ~50% of cells in local regions of the substrate (~1 mm2 areas) being GFP+. The expression of the GFP by those cells demonstrated the continued viability of the nanofiber penetrated cells on the substrate.

In the exemplary embodiments described herein, the cells are forced onto the penetrant structure by means of an external force. Forcing the cells onto the penetrant structures may be accomplished by contacting the substrate containing the penetrant structures with a solution of cells in a centrifuge tube and centrifuging briefly to apply enough force for the cells to become mounted on the structure. Additionally, the cells may be pressed onto the structures by pressing the substrate against a wetted substantially flattened surface containing a solution of the cells.

It will be appreciated that the embodiments of the disclosure may be used in a wide variety of applications where immobilization of biological cells is required. For example, a bioreactor may be constructed by a growing a plurality of cell penetrant structures in predetermined locations on a substrate. Extracellular component may be attached to each of the cell penetrant structures, wherein the component provides a function necessary for the survival of a biological cell. Biological cells useful in a bioreactor synthesis process may be penetrated by the cell penetrant structures so that the structures and the component are disposed in an intracellular domain of the biological cell. The growth and survival of a biological cell is maintained on the substrate to provide the bioreactor. A plurality of substrates having the same or different functions may be combined to provide bioreactors with additional functionality.

The foregoing embodiments are susceptible to considerable variation in its practice. Accordingly, the embodiments are not intended to be limited to the specific exemplifications set forth hereinabove. Rather, the foregoing embodiments are within the spirit and scope of the appended claims, including the equivalents thereof available as a matter of law.

The patentees do not intend to dedicate any disclosed embodiments to the public, and to the extent any disclosed modifications or alterations may not literally fall within the scope of the claims, they are considered to be part hereof under the doctrine of equivalents.

The invention claimed is:

1. An apparatus for transient biological transformation of a cell comprising:

an elongated cell penetrant structure having a penetrating tip with an opening, the elongated cell penetrant structure comprising a carbon nano-fiber core and a sheath present on exterior sidewalls of the carbon nano-fiber core, wherein the carbon-fiber core is recessed within the sheath to provide a compartment within the cell penetrant structure, the base of the compartment being defined by the carbon nano-fiber core and sidewalls of the compartment being defined by interior sidewalls of the sheath extending from the carbon fiber core to the opening of the penetrating tip, and wherein the elongated cell penetrant structure and penetrating tip are of such dimensions that said cell can be impaled therewith without being killed; and a substrate connected to a portion of the elongated cell penetrant structure opposite from the penetrating tip, wherein the base of the compartment is separated from the substrate by the carbon nano-fiber core.

2. The apparatus of claim 1 further comprising an array containing a multiplicity of said cell penetrant structure connected to a substrate at a location opposite from the penetrating tip.

3. The apparatus of claim 1 wherein an interior surface of the compartment contains elements selected from the group consisting of nitrogen and oxygen.

4. The apparatus of claim 1 wherein a surface of the cell penetrant structure possesses a coating selected from the group consisting of Au, Ag, Ni, Pt, silicon nitride, silicon dioxide, and polypyrrole.

5. An apparatus for transient biological transformation of a cell, the apparatus comprising:

a substrate;

an array of elongated cell penetrant structures disposed on the substrate in a substantially orthogonal orientation to the substrate, wherein each cell penetrant structure has a penetrating tip and an opening thereon leading to a compartment within the cell penetrant structure, wherein the cell penetrant structure comprises a carbon nano-fiber core and a sheath present on sidewall surfaces of the carbon nano-fiber core, in which a base of the compartment is provided by a recessed surface of the carbon nano-fiber core and the sidewalls of the compartment are provided by a portion of the sheath that extends beyond the recessed surface of the carbon nano-fiber core to provide the opening of the cell penetrant structure, wherein the sheath that is present around the sidewall surfaces of the carbon nano-fiber core is a coating selected from the group consisting of Au, Ag, Ni, Pt, silica, silicon nitride, silicon dioxide and polypyrrole.

6. The apparatus of claim 1 further comprising a biologically active component inside the compartment, wherein said biologically active component is precluded from escaping from the compartment when said compartment is inside a cell.

7. The apparatus of claim 6 wherein the biologically active component comprises a molecule selected from the group consisting of DNA, RNA, polypeptides, and enzymes.

8. The apparatus of claim 6, wherein the biologically active component is fixedly attached to an interior surface of the compartment.

9. The apparatus of claim 8 wherein the biologically active component is fixedly attached by at least one covalent bond between the biologically active component and an interior surface of the compartment.

10. The apparatus of claim 6, wherein the biologically active component is entrapped within the compartment.

11. The apparatus of claim 10 wherein the biologically active component is entrapped within the compartment by covering the opening at the penetrating tip with a semipermeable membrane.

12. The apparatus of claim 9, wherein said at least one covalent bond is directly between the biologically active component and internal surface of the compartment without a linking group.

13. The apparatus of claim 6, wherein the biologically active component includes one or more primary amines.

14. The apparatus of claim 8, wherein the biologically active component is fixedly attached to the interior surface of the compartment by one or more amide bonds resulting from condensation of one or more primary amines of the biologically active component and one or more carboxylic acid groups on the interior surface of the compartment.

15. The apparatus of claim 9, wherein said at least one covalent bond includes a linking group between the biologically active component and interior surface of the compartment.

16. The apparatus of claim 8 wherein the biologically active component is fixedly attached by one or more non-covalent interactions.

17. The apparatus of claim 1 wherein the elongated cell penetrant structure is conical-shaped.

18. The apparatus of claim 3 wherein the interior surface of the compartment contains carboxylic acid groups.

19. The apparatus of claim 5, wherein the carbon nano-fiber core is composed of substantially pure carbon and the sheath is composed of nitrogen doped carbon.

20. The apparatus of claim 5, wherein the carbon nano-fiber core comprises a conically shaped fiber having a length ranging from about 6 μm to about 10 μm.

21. The apparatus of claim 5, wherein the carbon nano-fiber core has a tip diameter at the penetrating tip ranging from about 20 nm to about 50 nm.

22. The apparatus of claim 5, wherein the compartment has an inner diameter of about 50 nm and an outer diameter of about 100 nm.

23. An apparatus for transient biological transformation of a cell comprising:

an elongated cell penetrant structure comprising carbon and having a penetrating tip and an opening thereon leading to a compartment within the cell penetrant structure, the compartment containing a biologically active component that is precluded from escaping from the compartment when said compartment is inside said cell, wherein the elongated cell penetrant structure and penetrating tip are of such dimensions that said cell can be impaled therewith without being killed; and a substrate connected to a portion of the elongated cell penetrant structure opposite from the penetrating tip.

* * * * *